US009145580B2

(12) United States Patent
Feehery et al.

(10) Patent No.: US 9,145,580 B2
(45) Date of Patent: *Sep. 29, 2015

(54) METHODS AND COMPOSITIONS FOR ENRICHING EITHER TARGET POLYNUCLEOTIDES OR NON-TARGET POLYNUCLEOTIDES FROM A MIXTURE OF TARGET AND NON-TARGET POLYNUCLEOTIDES

(71) Applicant: New England Biolabs, Inc., Ipswich, MA (US)

(72) Inventors: George R. Feehery, West Newbury, MA (US); Fiona Stewart, Ipswich, MA (US); James McFarland, Beverly, MA (US); Sriharsa Pradhan, Wenham, MA (US)

(73) Assignee: New England Biolabs, Inc., Ipswich, MA (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/834,142

(22) Filed: Mar. 15, 2013

(65) Prior Publication Data

US 2013/0189674 A1 Jul. 25, 2013

Related U.S. Application Data

(63) Continuation-in-part of application No. 13/435,590, filed on Mar. 30, 2012.

(60) Provisional application No. 61/471,134, filed on Apr. 2, 2011, provisional application No. 61/537,761, filed on Sep. 22, 2011, provisional application No. 61/598,715, filed on Feb. 14, 2012, provisional application No. 61/599,253, filed on Feb. 15, 2012.

(51) Int. Cl.
*C12Q 1/68* (2006.01)
*C07H 21/00* (2006.01)

(52) U.S. Cl.
CPC .................... *C12Q 1/6806* (2013.01)

(58) Field of Classification Search
CPC ............ C12Q 1/68; C07H 21/00; G01N 1/34; C12N 15/1003; C12N 15/1006; C12N 15/1013
USPC .................... 435/6.1; 536/22.1, 25.4
See application file for complete search history.

(56) References Cited

U.S. PATENT DOCUMENTS

| | | | |
|---|---|---|---|
| 4,683,194 A * | 7/1987 | Saiki et al. ............... | 435/6.12 |
| 4,769,061 A * | 9/1988 | Comai .................... | 504/206 |
| 4,946,952 A * | 8/1990 | Kiefer .................. | 536/25.41 |
| 5,242,823 A * | 9/1993 | Fareed et al. ............ | 435/252.3 |
| 6,239,116 B1 * | 5/2001 | Krieg et al. ............. | 514/44 A |
| 6,245,545 B1 * | 6/2001 | Kong et al. ............. | 435/199 |
| 7,670,773 B2 | 3/2010 | Minassian et al. | |
| 8,206,935 B2 * | 6/2012 | Li et al. ................. | 435/7.1 |
| 8,367,331 B2 * | 2/2013 | Feehery et al. .......... | 435/6.1 |
| 2005/0233364 A1 * | 10/2005 | Burgess et al. .......... | 435/6 |
| 2007/0231800 A1 * | 10/2007 | Roberts et al. .......... | 435/6 |
| 2008/0075755 A1 * | 3/2008 | Deschatelets et al. ..... | 424/427 |
| 2008/0220433 A1 * | 9/2008 | Ahlquist et al. ......... | 435/6 |
| 2008/0260743 A1 * | 10/2008 | Rehli .................... | 424/139.1 |
| 2009/0123914 A1 * | 5/2009 | Erikson et al. .......... | 435/6 |
| 2009/0246784 A1 * | 10/2009 | Sakai et al. ............ | 435/6 |
| 2010/0316993 A1 * | 12/2010 | Schmidt et al. ......... | 435/6 |
| 2012/0122087 A1 * | 5/2012 | Li et al. ................ | 435/6.11 |
| 2014/0045183 A1 * | 2/2014 | Okamoto et al. ........ | 435/6.11 |
| 2014/0057877 A1 * | 2/2014 | Murphy et al. ......... | 514/107 |
| 2014/0178873 A1 * | 6/2014 | Brachmann et al. ..... | 435/6.11 |
| 2014/0178881 A1 * | 6/2014 | Booth et al. ........... | 435/6.11 |
| 2014/0272968 A1 * | 9/2014 | Gundling et al. ....... | 435/6.11 |

FOREIGN PATENT DOCUMENTS

WO  WO2004/033683  *  4/2004

OTHER PUBLICATIONS

Ames, B. Endogenous DNA damage as related to cancer and aging. Mutation Research 214 (1) :41 (1989).*
Hakonen et al.,Mitochondrial DNA Polymerase W748S Mutation: A Common Cause of Autosomal Recessive Ataxia with Ancient European Origin. American Journal of Human Genetics 77 :430 (2005).*
Holt et al.Deletions of muscle mitochondrial DNA in mitochondrial myopathies: sequence analysis and possible mechanisms. Nucleic Acids Research 17 (12) : 4465 (1989).*
Hudson et al. The Use of an Ethidium Analogue in the Dye-Buoyant Density Procedure for the Isolation of Closed Circular DNA: The Variation of the Superhelix Density of Mitochondrial DNA. PNAS 62(3) : 813 (1969).*
Shmookler et al., Mitochondrial DNA in Mortal and Immortal Human Cells : Genome Number, Integrity, and Methylation Journal of Biological Chemistry 258 (15) :9078 (1983).*
Szwagierczak et al.Sensitive enzymatic quantification of 5-hydroxymethylcytosine in genomic DNA . Nucleic Acids Research 38(19) : e181 (1910).*
Yakes et al.Mitochondrial DNA damage is more extensive and persists longer than nuclear DNA damage in human cells following oxidative stress. PNAS 94 :514 (1997).*

(Continued)

*Primary Examiner* — Ethan C Whisenant

(74) *Attorney, Agent, or Firm* — New England Biolabs, Inc; Hariet M. Strimpel; D. Phil

(57) ABSTRACT

Compositions and methods are provided for enriching mitochondrial DNA and optionally chloroplast DNA from eukaryotic cells in a simple rapid method that provides greater than 100 fold enrichment. Affinity protein-coated substrate in a buffer is used to efficiently bind chromosomal DNA and thereby remove it from the buffer. Mitochondrial sequencing reads reveal that non-biased sequence selection providing representation of a substantial proportion of mitochondrial DNA in the eukaryotic cells analyzed.

21 Claims, 15 Drawing Sheets

(56) References Cited

OTHER PUBLICATIONS

Asakawa et al. Human BAC library: construction and rapid screening. Gene 191 : 69 (1997).*
Cross et al., Purification of CpG islands using a methylated DNA binding column. Nature Genetics 6:236 (1994)—http://www.nature.com/ng/journal/v6/n3/pdf/ngO394-236.pdf.*
Ehrlich et al. Amount and distribution of 5-methylcytosine in human DNA from different types of tissues or cells. Nucleic Acids Research 10 (8) : 2709 (1982).*
Ehrlich et al. 5-Methylcytosine in Eukaryotic DNA. Science 212 :1350 (1981).*
Grosveld et al. The construction of cosmid libraries which can be used to transform eukaryotic cells. Nucleic Acids Research 10 (21):6715 (1982).*
Hakonen et al.,Mitochondrial DNA Polymerase W748S Mutation: A Common Cause of Autosomal Recessive Ataxia with Ancient European Origin. American Journal of Human Genetics 77:430 (2005).*
Murray et al., Rapid Isolation of High Molecular Weight Plant DNA. Nucleic Acids Research 8(19) : 4321 (1980).*
Shmookler et al. Mitochondrial DNA in Mortal and Immortal Human Cells J. of Biological Chemistry 258 (15) :9078 (1983).*
Szwagierczak et al.Sensitive enzymatic quantification of 5-hydroxymethylcytosine in genomic DNA. Nucleic Acids Research 38(19) e181 (2010).*
Yakes et al., Mitochondrial DNA damage is more extensive and persists longer than nuclear DNA damage in human cells following oxidative stress. PNAS 94:514 (1997).*
Wu, et al. Lab Chip, 9:1193-1199 (2009).
Horz, et al., Anaerobe 16:47-53 (2010).
Dewhirst et al. J. Bacterol, 192(19):5002-17 (2010).
Voo, et al., Mol Cell Biol. 20(6): 2108-2121 (2000).
Pradhan, S. et al., J. Biol. Chem., 274, 33002-33010 (1999).
Qian, J. Biol. Chem. 283: 34490-34494 (2008).
Sambrook et al., Molecular Cloning: A Laboratory Manual, 3rd ed. pp. 6.4-6.11, Cold Spring Harbor Lab Press, Cold Spring Harbor, NY, 2001.

* cited by examiner

FIG. 6B

BACTERIA LEGION

1 Prevotella melaninogenica
2 Veillonella atypica
3 Streptococcus pneumoniae
4 Neisseria sicca
5 Streptococcus mitis
6 Streptococcus oralis
7 Rothia mucilaginosa
8 Prevotella veroralis
9 Neisseria sp. oral taxon 014
10 Streptococcus sp. oral taxon 071
11 Veillonella parvula
12 Streptococcus parasanguinis
13 Granulicatella adiacens
14 Megasphaera micronuciformis
15 Haemophilus influenzae
16 Rothia dentocariosa
17 Prevotella sp. oral taxon 299
18 Oribacterium sinus
19 Neisseria flavescens
20 Prevotella oris
21 Streptococcus gordonii
22 Aggregatibacter aphrophilus
23 Neisseria elongata
24 Campylobacter concisus
25 Neisseria meningitidis
26 Catonella morbi
27 Granulicatella elegans
28 Streptococcus salivarius
29 Leptotrichia hofstadii
30 Prevotella sp. oral taxon 472
31 Prevotella bivia
32 Neisseria gonorrhoeae
33 Streptococcus vestibularis
34 Prevotella tannerae
35 Prevotella marshii
36 Prevotella buccae
37 Capnocytophaga ochracea
38 Atopobium parvulum
39 Streptococcus agalactiae
40 Prevotella buccalis
41 Leptotrichia buccalis
42 Fusobacterium periodonticum
43 Capnocytophaga gingivalis
44 Neisseria polysaccharea
45 Prevotella sp. oral taxon 317
46 Escherichia coli
47 Enterococcus faecalis
48 Streptococcus pyogenes
49 Simonsiella muelleri
50 Cardiobacterium hominis
51 Aggregatibacter actinomycetemcomitans
52 Fusobacterium nucleatum
53 Kingella oralis
54 Selenomonas sp. oral taxon 149
55 Porphyromonas uenonis
56 Bacteroidetes oral taxon 274
57 Haemophilus ducreyi
58 Abiotrophia defectiva
59 Porphyromonas endodontalis
60 Dialister invisus
61 Pseudomonas aeruginosa
62 Streptococcus infantarius
63 Peptostreptococcus stomatis
64 Selenomonas flueggei
65 Filifactor alocis
66 Lactococcus lactis
67 Streptococcus downei
68 Shuttleworthia satelles
69 Yersinia pestis
70 Peptoniphilus sp. oral taxon 836
71 Campylobacter showae
72 Pseudomonas stutzeri
73 Peptostreptococcus anaerobius
74 Leptotrichia goodfellowii
75 Finegoldia magna
76 Selenomonas noxia
77 Oribacterium sp. oral taxon 078
78 Campylobacter gracilis
79 Mycobacterium tuberculosis
80 Staphylococcus aureus
81 Staphylococcus epidermidis
82 Eubacterium yurii
83 Acinetobacter baumannii
84 Bacillus anthracis
85 Bulleidia extructa
86 Actinomyces sp. oral taxon 848
87 Mesorhizobium loti
88 Peptoniphilus sp. oral taxon 386
89 Mobiluncus mulieris
90 Cryptobacterium curtum
91 Delftia acidovorans
92 Listeria monocytogenes
93 Achromobacter xylosoxidans
94 Bordetella pertussis
95 Peptoniphilus lacrimalis
96 Lactobacillus salivarius
97 Campylobacter curvus
98 Klebsiella pneumoniae
99 Bacillus subtilis
100 Propionibacterium acnes
101 Anaerococcus tetradius
102 Scardovia inopinata
103 Agrobacterium tumefaciens
104 Proteus mirabilis
105 Corynebacterium diphtheriae
106 Arcanobacterium haemolyticum
107 Stenotrophomonas maltophilia
108 Variovorax paradoxus
109 Enterococcus casseliflavus
110 Lactobacillus johnsonii
111 Cronobacter sakazakii
112 Lactobacillus gasseri
113 Treponema vincentii
114 Lactobacillus reuteri
115 Lactobacillus iners
116 Gardnerella vaginalis
117 Moraxella catarrhalis
118 Ochrobactrum anthropi
119 Lactobacillus casei
120 Helicobacter pylori
121 Lactobacillus rhamnosus
122 Anaerococcus prevotii
123 Olsenella uli
124 Slackia exigua
125 Lactobacillus fermentum
126 Atopobium vaginae
127 Eubacterium saphenum
128 Lysinibacillus fusiformis
129 Staphylococcus warneri
130 Lactobacillus crispatus
131 Lactobacillus brevis
132 Lactobacillus jensenii
133 Bifidobacterium dentium
134 Bacillus clausii
135 Stenotrophomonas sp. SKA14
136 Lactobacillus acidophilus
137 Lactobacillus paracasei
138 Lactobacillus coleohominis
139 Mycobacterium leprae
140 Eggerthella lenta
141 Lactobacillus oris
142 Parascardovia denticolens
143 Paenibacillus sp. oral taxon 786
144 Pyramidobacter piscolens
145 Chlamydia pneumoniae
146 Treponema pallidum
147 Lactobacillus vaginalis
148 Mycoplasma hominis
149 Jonquetella anthropi
150 Mycoplasma genitalium
151 Mycoplasma fermentans

US 9,145,580 B2

METHODS AND COMPOSITIONS FOR ENRICHING EITHER TARGET POLYNUCLEOTIDES OR NON-TARGET POLYNUCLEOTIDES FROM A MIXTURE OF TARGET AND NON-TARGET POLYNUCLEOTIDES

CROSS REFERENCE

This application is a continuation-in-part of U.S. patent application Ser. No. 13/435,590, filed Mar. 30, 2012 which claims priority from the following U.S. provisional application Nos. 61/471,134, filed Apr. 2, 2011; 61/537,761, filed Sep. 22, 2011; 61/598,715, filed Feb. 14, 2012; and 61/599,253, filed Feb. 15, 2012.

BACKGROUND

Viruses, bacterial, yeast and eukaryotic multicellular organisms may coexist in complex associations in nature. An example of this type of association is that of microbiomes, which inhabit mammalian hosts. Rapid DNA sequencing techniques have been used to investigate microbiomes. The accuracy of the species identification has been adversely affected by uncertainty concerning the presence and amount of mammalian genomic DNA in the samples that affect the signal to noise ratio. This is particularly problematic in those situations where the DNA of interest is present in very small amounts amidst a high background of host genomic material.

Zhigang Wu, et al. (*Lab Chip*, 9:1193-1199 (2009)) developed a microfluidic device to physically separate bacterial cells from human blood cells based on soft inertial force-induced migration using flow-defined, curved and focused sample flow inside a microfluidic device resulting in 300-fold enrichment of bacteria. This type of cell separation can only reduce background contamination of the DNA between two types of cells if the cells are viable.

Another method used to isolate DNA from sepsis-causative bacteria in blood relies on the selective lysis of human-nucleated cells using a chaotropic reagent (MolYsis, Molzym GmbH, Bremen, Germany). This method also relies on viable cells. A salt-resistant DNase was used to degrade human DNA from lyzed cells, while intact bacterial cells were unaffected by DNAse. The DNAse was then inactivated and the bacterial DNA extracted and purified for analysis. The technique reduces the total human DNA concentration in the sample by 99.5%. However, total bacterial DNA recovery was low at only 30% of the expected total (Horz, et al., *Anaerobe* 16:47-53 (2010)).

At present, there is no satisfactory method for enriching target DNA from an environmental sample, which contains a mixture of DNAs under conditions in which loss of target DNA is minimized and viable cells as a source of DNA are not a requirement.

SUMMARY

In general in one aspect, a composition is provided that includes eukaryotic cell DNA containing chromosomal DNA and mitochondrial DNA that may be obtained from a lysate of a cell culture, cell line, biopsy, fractionated blood, tissue from a unicellular or multicellular plant or animal or any other source, a matrix coated with methyl binding domain peptide for selectively binding chromosomal DNA and a buffer containing effective amounts of a salt and a non-ionic detergent. Examples of a matrix includes a two or three dimensional material which may be for example, a bead, a column, or a porous matrix. Examples of a methyl binding domain peptide includes UHRF1(SRA), CXX1, DNMT1, MBD or methyl-binding variants thereof. The buffer includes any formulation that enhances the binding of DNA containing methylcytosine, hydroxymethylcytosine or other modified base and may include 10 mM-800 mM salt.

An embodiment includes a composition in which the total cell DNA is fractionated so that the chromosomal DNA binds to the methyl binding domain while mitochondrial DNA and/or chloroplast DNA and/or prokaryotic DNA is unbound and concentrated in the buffer as a supernatant. For example, the concentration of unbound mitochondrial DNA, chloroplast DNA, bacterial DNA and/or viral DNA in the buffer may be greater than 5 fold, 10 fold, 20 fold, 30 fold, 40 fold, 50 fold, 60 fold, 70 fold, 80 fold, 90 fold, 100 fold, 110 fold or 120 fold compared with an amount in the eukaryotic cell DNA prior to enrichment in the presence of the matrix coated with the methyl binding domain. Chloroplast DNA is about ten times larger than mitochondrial DNA so that a 5 fold increase in chloroplast DNA in the buffer (supernatant) can facilitate sequencing of the chloroplast DNA while avoiding contamination of genomic DNA.

An embodiment includes an unbound fraction containing more than 80%, 85%, 90%, or 95% of total mitochondrial DNA in the eukaryotic cell DNA or 80%, 85%, 90%, or 95% of total mitochondrial and chloroplast DNA in the eukaryotic cell DNA. The buffer may also include less than 20%, 15%, 10% or 5% unbound chromosomal DNA of the total chromosomal DNA present in the eukaryotic cell DNA.

In general in one aspect, a method is provided for enriching cellular mitochondrial DNA from eukaryotic cell DNA, that includes combining the eukaryotic cell DNA with a matrix coated with methyl binding domain peptide for selectively binding chromosomal DNA and a buffer containing effective amounts of a salt and a non-ionic detergent; permitting binding of chromosomal DNA to methyl binding domain coated magnetic beads; and obtaining an enriched preparation of mitochondrial DNA in the buffer.

Embodiments of the methods may include one or more additional steps such as: determining the fraction of mitochondrial DNA and chromosomal DNA in the supernatant; sequencing a part of the entire mitochondrial DNA; performing a genetic analysis of the mitochondrial DNA; and/or analyzing the mitochondrial DNA for oxidative damage.

Embodiment of the methods may include one or more additional features such as the methyl-binding domain (MBD) being selected from the group consisting of UHRF1 (SRA), CXX1, DNMT1, MBD or methyl-binding variants thereof; the affinity matrix being comprised of magnetic beads; and/or the magnetic beads are coated with protein A bound to MBD2a-Fc.

In general in one aspect, a method for detecting oxidative damage in mitochondrial DNA is provided that includes (a) enriching mitochondrial DNA (b) identifying a change in oxidation status of methylcytosine to hydroxymethylcytosine in chromosomal DNA bound to the MBD as an indicator; and (c) analyzing the mitochondrial DNA in the supernatant for reactive oxygen damage.

BRIEF DESCRIPTION OF THE DRAWINGS

FIG. 3A shows samples tested using no beads (c) or 20 µl or 40 µl (200 µg/ml) MBD beads. The genomic DNA from left to right was purified from: Jurkat 2, HCT 116 1, HCT 116 2, FIG. 3B shows samples tested using no beads (c) or 20 µl or 40 µl (200 µg/ml) MBD beads. The genomic DNA from left to right was purified from:IMR 90, 3T3 Mouse, Hela and Jurkat 1 cell lines. Effective removal of these DNAs was achieved with 20 µl of the MBD beads for IMR 90 cells and 40 µl of the MBD beads for the other cell types.

FIG. 3C shows that greater than 92% of the mammalian genomic DNA in a single sample (with a mean of 97% for all samples tested) was removed by the MBD beads while at least 80% of *E. coli* DNA with a mean of 90% remained in the supernatant when compared with the starting amount.

FIGS. 6A-1, 6A-2 and 6B show the improvement in efficiency in analyzing a microbiome from a human saliva sample using MBD beads to provide enrichment of the bacterial DNA by removal of the host DNA compared with the results obtained in the absence of MBD bead enrichment.

FIG. 6A-1 and 6A-2 show sequencing reads mapped to 150 known oral microbes (numbered 1-150 on the x-axis) before and after enrichment. The reads were aligned to 150 different bacterial species specified in the HOMD using Bowtie 0.12 alignment software (Langmead et al. *Genome Biology* 10:R25 (2009). doi:10.1186/gb-2009-10-3-r25). Overall, the number of aligned reads from the enriched sample increased 10-fold, with no loss of species diversity.

FIG. 6B provides the bacterial species corresponding to the numbers on the X-axis of the graph in FIG. 6A.

FIG. 8A shows that the amount of chromosomal DNA was substantially reduced in the supernatant after MBD treatment.

(−) is prior to treatment and (+) is after treatment where 1=heart; 2=fetal brain; 3=old brain; 4=Alzheimer brain; 5=MS brain; 6=Demential brain FIG. 8B shows the extent of enrichment of mitochondrial DNA in the supernatant fraction determined by qPCR analysis of the mitochondria cytochrome b (CYTB) gene. Overall, 96% of human chromosomal DNA was removed from by the MBD beads, while 95% of mitochondrial DNA remained in the supernatant.

FIG. 9A shows the results of Illumina MiSeq Sequencing of supernatant DNA from a human female fetal lung fibroblast (IMR90) obtained using the protocol of FIG. 7. The fraction of total reads for each chromosome of the unenriched and enriched samples was determined. A 124 fold increase in reads mapped to mitochondrial DNA is shown.

FIG. 9B shows the fraction of total DNA reads from unenriched total DNA, and enriched supernatent.

FIG. 9C is a table reporting the total number of reads and the ratio of total reads to mitochondria reads in unenriched, enriched and MBD bound fractions.

FIG. 10A shows (1) a map of the mitochondrial genome, (2) the read coverage of unenriched mitochondrial DNA (55,000 reads), (3) read coverage of enriched mitochondrial DNA (55,000 reads) and (4) read coverage of enriched mitochondrial DNA (530,0000 reads corresponding to the full data set of reads). The profile of the reads were preserved in all analyses confirming that the enrichment step does not introduce bias into the analysis of mitochondrial DNA.

FIG. 10B shows average coverage of the enriched data set by the distribution of reads of the different chromosomes in a mammalian cell. The mitochondrial DNA is enriched by 160 fold in this example compared with the unenriched sample.

Figure 1:
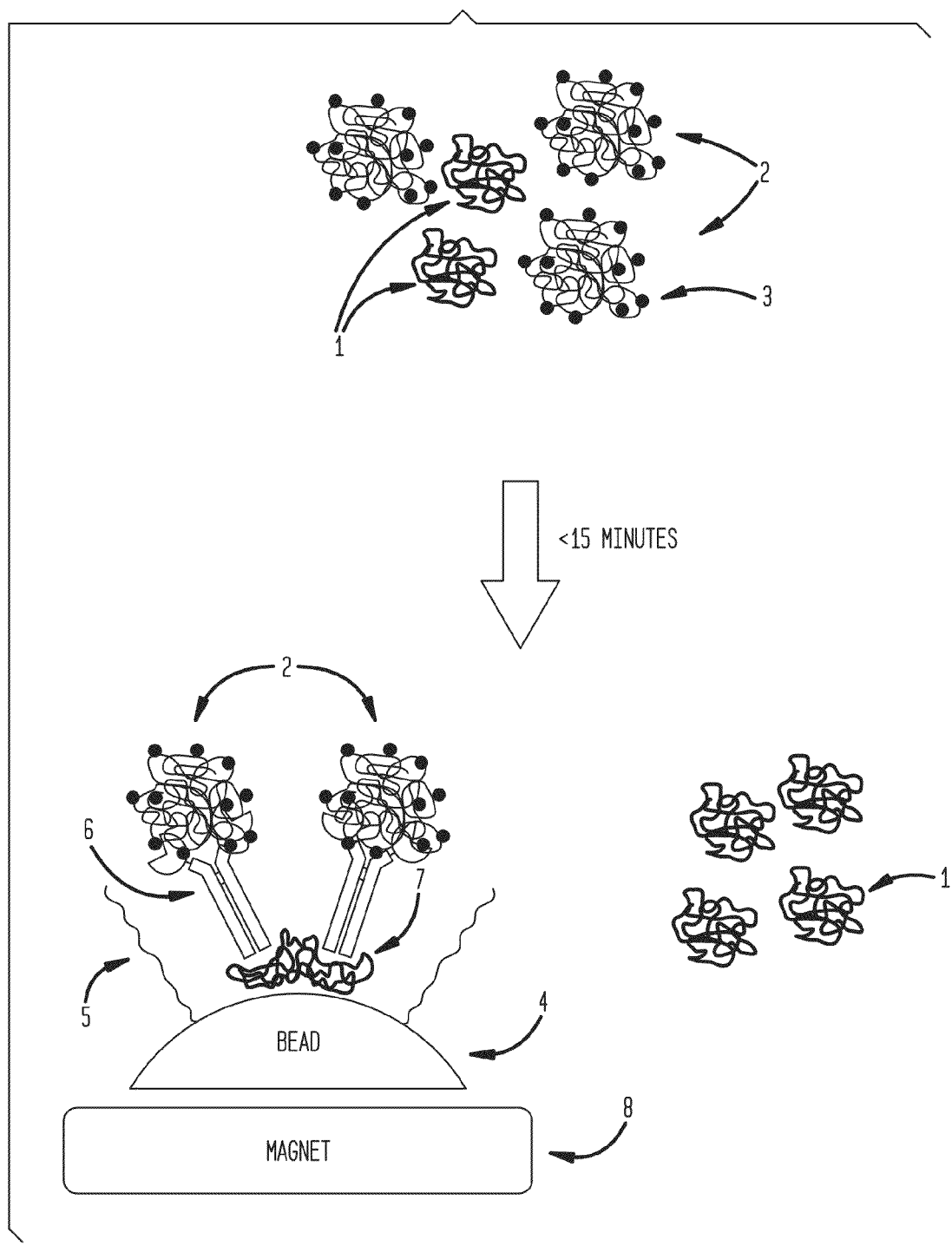
FIG. 1 shows a schematic workflow for enrichment of target DNA in a mixture of target DNA (1) and non-target DNA (2) containing 5-methyl CpG (3). (1) and (2) are mixed with magnetic beads (4), which have been coated with protein A (7) to which methyl-binding domain (MBD2A) is fused to Fc (6) to form MBD2A-Fc beads in the presence of a non-ionic detergent (5). Eukaryotic genomic DNA (3) becomes bound to the MBD beads (4). A magnet (8) attracts the non-target DNA bound to the MBD beads leaving target DNA (1) in the supernatant.

Additional embodiments are described in the parent patent application Ser. No. 13/435,590 and are incorporated by reference.

DETAILED DESCRIPTION OF THE EMBODIMENTS

A "target" polynucleotide may refer to a polynucleotide having a particular desired feature where this feature may be a modification on a nucleoside in the polynucleotide. A "non-target" polynucleotide lacks this feature. The desired feature may render the target polynucleotide capable of specific binding to an affinity domain immobilized on a solid support or matrix.

An example of target polynucleotides includes a mammalian genomic DNA that naturally contains a modified base, for example, methylated cytosine where the modified base may occur at a density of greater than 1/200 bases. An example of non-target polynucleotides include bacterial DNA, mitochondrial DNA, chloroplast DNA and viral DNA all of which do not include 5-mC (modified base found in eukaryotic cells) or else contain the modified base at a density of less than 1/200 bases. In certain contexts, it may be desirable to efficiently obtain selected DNA having other modified bases, where the modified bases occur at a density which enables the DNA to be enriched from a mixture of DNA including under-modified or unmodified DNA while in the other contexts, under-modified or unmodified DNA is of particular interest and may be preferentially recovered for further analysis.

A "modified" polynucleotide is a polynucleotide containing at least one specific base that differs from A, G, T or C by an addition of a side group such as a methyl group, hydroxymethyl, 5-formylmethyl, or carboxymethyl. A modified cytosine, in particular a methylated cytosine is the most commonly occurring modification in a eukaryotic genome and binds to MBD. Examples of other modified bases include: N-6 methyladenine and N-4 methylcytosine. The modified base can be further derivatized to include a tagging reagent, which could then be captured by an affinity agent. For example, 5-hmC could be glucosylated with a modified glucose, with the modified glucose containing biotin.

Embodiments of the invention provide methods for separating a target polynucleotide from non-target polynucleotide. These methods achieve polynucleotide enrichment by utilizing naturally occurring differences in the density of modified nucleotides (for example methylated cytosine in target DNA versus non-target DNA). For example, in order to sequence microbiome DNA, mitochondrial DNA, chloroplast DNA (non-target DNA), it is desirable to remove contaminating mammalian genomic DNA (target DNA) from a DNA mixture obtained from a biological sample (such as human-derived saliva, mucosa, blood or tissue biopsies). The difference in density of modified bases in the microbiome DNA, mitochondrial DNA or chloroplast DNA and the mammalian genomic DNA results in selective binding of the mammalian genomic DNA to an affinity matrix while the microbiome DNA/mitochondrial DNA/chloroplast DNA remains in the supernatant.

There are several hundred mitochondrial diseases that have been identified. In some cases, SNPs thought to be associated with mitochondria are actually present on chromosomes as a result of DNA translocation from mitochondrial DNA to chromosomal DNA at some time during evolution resulting in an incorrect assignment of a marker. Consequently, effective separation and enrichment of mitochondrial DNA is helpful in avoiding this type of confusion. The same can be true for chloroplast DNA. As shown in Example, 4 and FIGS. 7-11, the methods described herein were effective in enriching for mitochondrial DNA where the mitochondrial DNA did not bind to immobilized MBD.

Separation of target from non target DNA and enrichment of each DNA can be rapidly achieved by means of a brief incubation of tissue or cell DNA (for example, 10 or 15 minute incubation is sufficient although a longer or shorter incubation may be used) with MBD-fc protein A-magnetic beads. This substrate effectively binds human chromosomal DNA to remove it from a sample also containing bacterial, mitochondrial, chloroplast DNA and/or viral DNA thereby causing a concentration of the latter in the supernatant. This enrichment can increase reads in excess of 5 fold, for example, 10 fold, 20 fold, 30 fold, 40 fold, 50 fold, 60 fold, 70 fold, 80 fold, 90 fold, 100 fold, 110 fold, 120 fold or 150 fold in a robust and consistent manner. This technology has advantages over existing enrichment procedures that rely on PCR amplification or isothermal amplification techniques (such as rolling circle amplification) that introduce sequence errors and misalignments.

This approach has the advantage of being rapid and avoiding further purification steps to remove non-specifically bound target DNA from the affinity matrix. The enriched DNA can then be sequenced using standard techniques and the microbial content rapidly determined (see FIG. 6A.)

Parameters that were found to play a role in rapid, selective and specific enrichment of target and non-target polynucleotides include one or more of the following:

(a) Protein-coated Affinity-binding Matrix for Binding Modified Polynucleotides

An "affinity matrix" as used herein refers to a matrix which is associated with an affinity protein or domain for binding polynucleotides containing modified bases. In an embodiment of the invention, a bead, more particularly, a magnetic bead, was used as an affinity matrix where the type of magnetic bead was, for example, a carboxylated polystyrene bead (for example a Seradyn, bead from Thermo Scientific, Waltham, Mass.) or a carboxylated polyvinyl chloride bead (for example, from Chemagen, PerkinElmer, Waltham, Mass.), more particularly a polystyrene bead. The examples illustrate the use of affinity protein-coated magnetic polystyrene bead where the magnetic polystyrene beads are available from New England Biolabs, Inc. (NEB), Ipswich, Mass.

The affinity protein or domain includes, for example, antibodies such as protein A, restriction endonucleases such as PvuRtsII or modifications thereof, a glucosyl transferase domain and/or modified nucleoside-binding domains or variants thereof such as methyl-binding domains. Examples of affinity proteins having binding specificity for CpG-methylated cytosine in DNA or RNA include MeCP2, MBD1, MBD2, MBD3, or MBD4 (U.S. Pat. No. 7,670,773). These share a 70-residue MBD (U.S. Patent Application Publication No. 2008/0260743). Any of these proteins or variants thereof may be used to coat the beads described above and are here referred to as MBD. Other molecules capable of binding methylated cytosine in DNA include ribozymes or other polynucleotides, proteins such as antibodies, UHRF1 (SRA domain, domains such as from human UHRF1) or murine NP95, CXXC1, DNMT1 proteins and modifications thereof or variants of restriction endonucleases that no longer have cleavage activity but retain their DNA binding specificity (see for example, Qian, *J. Biol. Chem.* 283:34490-34494 (2008); Voo, et al., *Mol Cell Biol.* 20(6):2108-2121 (2000); Pradhan, et al., *J. Biol. Chem.*, 274:33002-33010 (1999)).

The above proteins may be linked to a spacer to project the binding protein away from the surface of the bead by a desired distance, which is determined by the polymer length of the non-ionic detergent used in the sample buffer.

The examples describe the use of "MBD beads". These are magnetic beads coated with protein A to which is bound MBD2a-Fc in a ratio of two molecules of MBD2a-Fc to one molecule of protein A.

MBD2a-Fc has an amino acid sequence as follows:

```
Human MBD2 [AA 144-230]
                                      (SEQ ID No. 1)
ESGKRMDCPALPPGWKKEEVIRKSGLSAGKSDVYYFSPSGKKFRSKP
QLARYLGNTVDLSSFDFRTGKMMPSKLQKNKQRLRNDPL.

Flexible Linker
                                      (SEQ ID No. 2)
AAADPIEGRGGGGG.

Human IgG1 [AA 99-330] Fc region
                                      (SEQ ID No. 3)
DPKSSDKPHTCPPCPAPELLGGPSVFLFPPKPKDTLMISRTPEVTCV
VVDVSHEDPEVKFNWYVDGVEVHNAKTKPREEQYNSTYRVVSVLTVL
HQDWLNGKEYKCKVSNKALPAPIEKTISKAKGQPREPQVYTLPPSRD
ELTKNQVSLTCLVKGFYPSDIAVEWESNGQPENNYKATPPVLDSDGS
FFLYSKLTVDKSRWQQGNVFSCSVMHEALHNHYTQKSLSLSPGK.
```

Embodiments of the method utilize MBD beads to efficiently and rapidly separate DNA from prokaryotes or mitochondria that contain little or no methylated CpGs, compared to mammalian DNA which contains about 4% methylated cytosine adjacent to a guanine (mCpG).

(b) Salt in the Buffer

The amount of salt in the buffer containing the mixture of polynucleotides and the affinity-binding matrix was found to determine the density of methylated bases in polynucleotides capable of binding to the affinity matrix described above. Salts suitable for the purpose of enrichment include NaCl, KCl, or other salts in the range of 10 mM-800 mM. An example is 150-450 mM NaCl.

Figure 2:
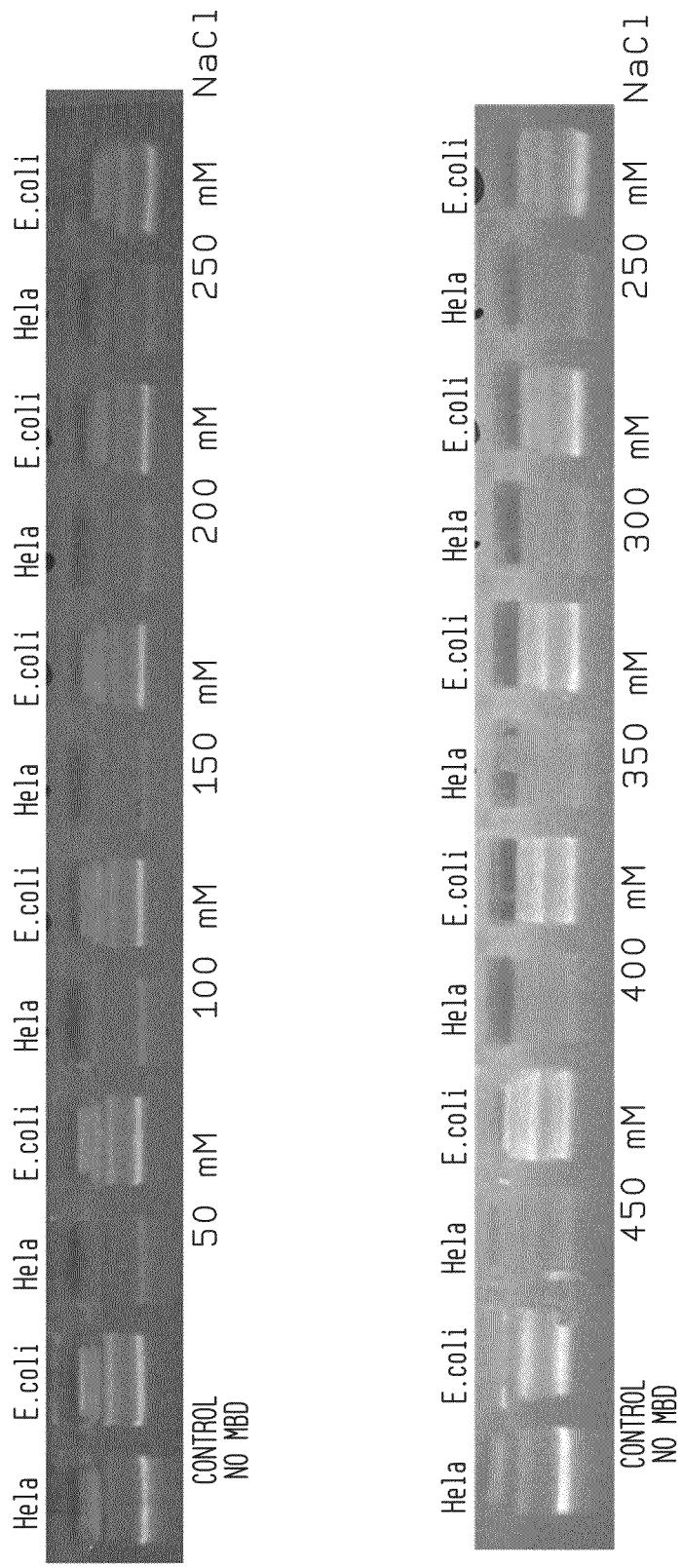
FIG. 2 shows the effect of NaCl on MBD beads pull down of methylated DNA. The bands on the gel correspond to DNA in the supernatant after the DNA from Hela cells or *E. coli* cells is mixed with MBD beads. The results are shown at different salt concentrations increasing from 50 mM to 450 mM in 50 mM increments. Some Hela DNA was seen in the supernatant up to 200 mM NaCl.
Figure 3:
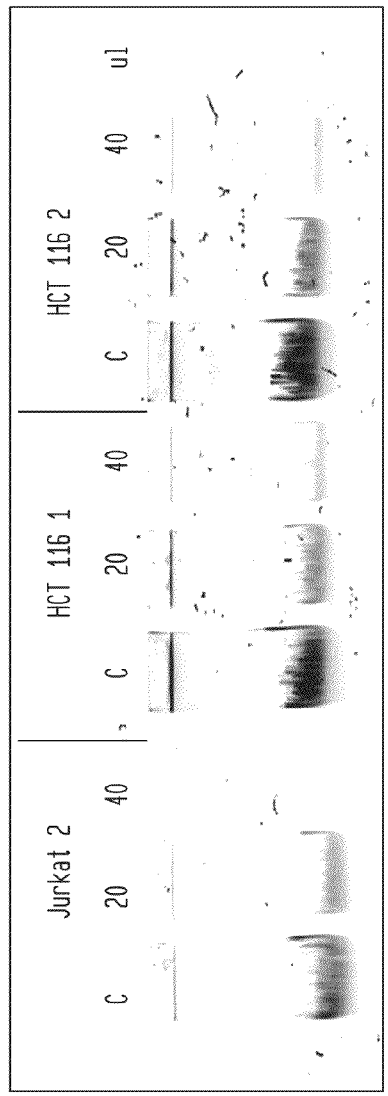
FIG. 3A-C shows the results obtained on a 1% agarose gel of the pull down of methylated DNA by MBD beads. 500 ng of purified mammalian genomic DNA and 50 ng of tritiated *E. coli* DNA having a size of 10 kb-20 kb were combined with varying amounts of MBD beads and the DNA recovered and analyzed on 1% agarose gels with SYBR® (Life Technologies, Carlsbad, Calif.) stain. Densitometry was used to determine the amount of mammalian DNA remaining in the supernatant after treatment with the varying concentrations of beads. The amount of *E. coli* DNA before and after mixing with beads was determined by scintillation counting.
Figure 3:
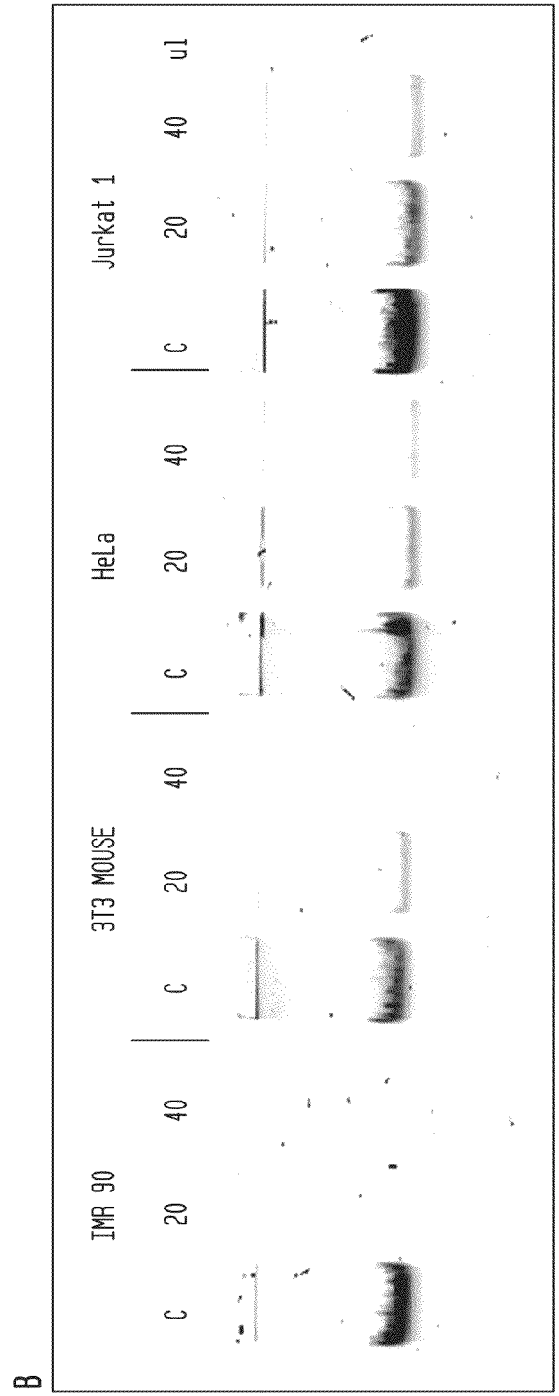
Figure 3C:
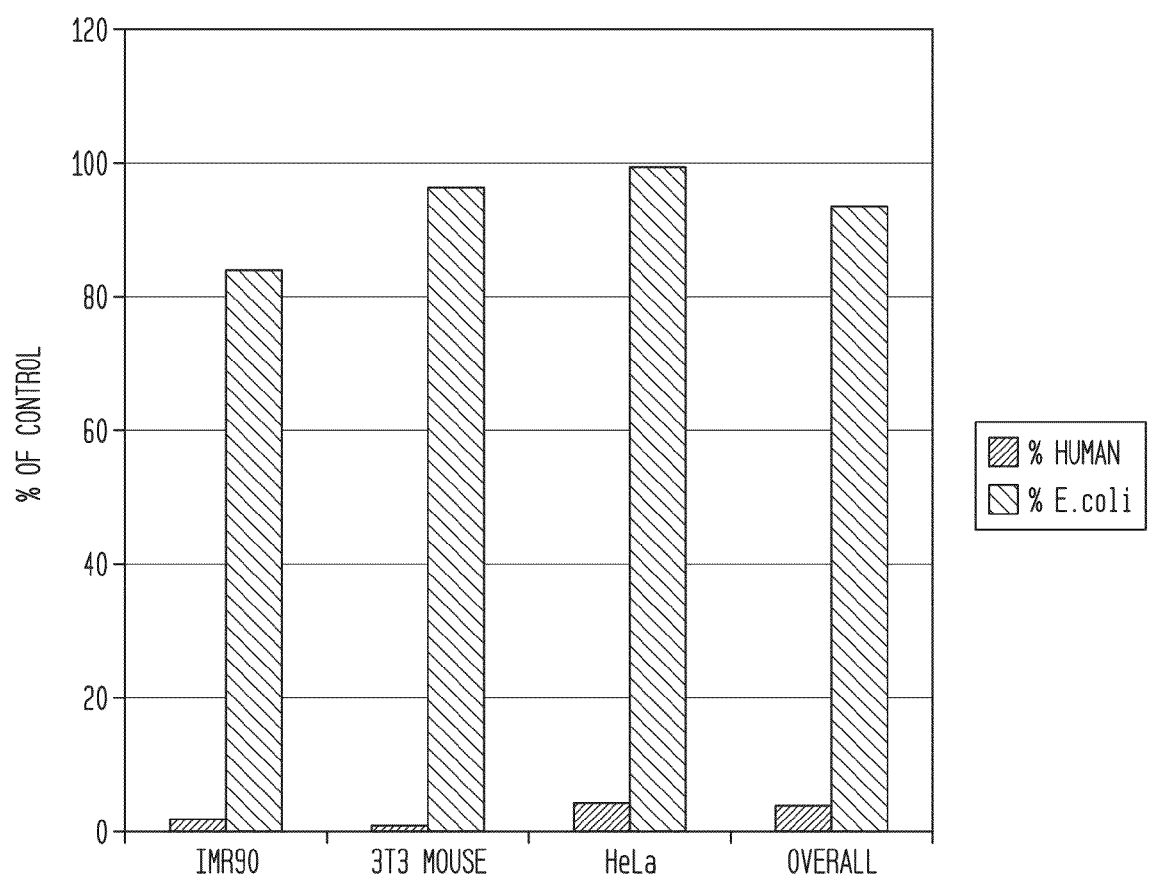
Figure 4:
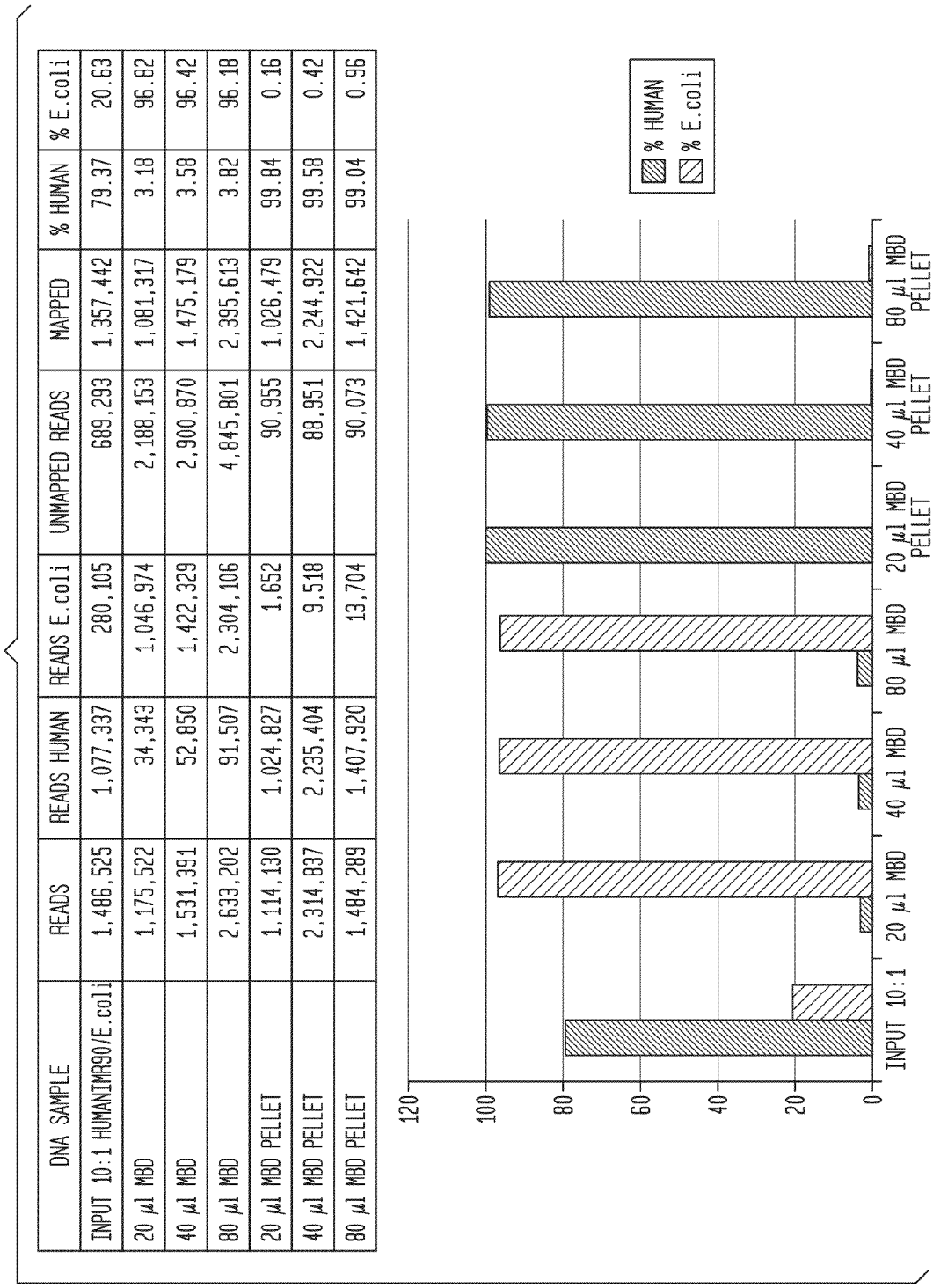
FIG. 4 shows the enrichment effect using different volumes of MBD beads (200 µg/ml) on a constant amount of human (IMR 90) and bacterial (*E. coli*) DNA (10:1) where the DNA fragments had a size of at least 20 kb. The supernatant was assayed on an Ion Torrent™ Personal Genome Machine (PGM)™ System (Life Technologies, Carlsbad, Calif.). The MBD bead-bound DNA was 99.5% human DNA as determined by aligned sequence reads while the aligned sequence reads of DNA in the supernatant was 96% *E. coli*. In the absence of MBD beads, the ratio of aligned sequence reads of human DNA to *E. coli* DNA was about 80% to about 20%.

Salt concentration can be varied as shown in FIG. 2 to determine the binding of polynucleotides containing a threshold amount of modified bases for the polynucleotides to bind to the affinity matrix. Here, the presence of salt exemplified by NaCl enhanced binding of modified DNA to the affinity matrix (MBD beads) resulting in the removal of host genomic DNA, as seen by the decrease in Hela DNA in the supernatant. For example, in the presence of 300 mM salt, only polynucleotide fragments with at least 3-fold to 6-fold more methylated CpGs than the unmodified DNA became bound to the affinity matrix. For human genomic polynucleotide fragments which are about 4% methylated, a 20 kb fragment would be expected to contain 800 methylated bases so that these polynucleotides readily bind to the affinity matrix in 300 mM salt. In contrast, polynucleotides that may have less than three methylated CpGs do not bind to the affinity matrix in this salt concentration.

(c) Non-ionic Detergent

While not wishing to be limited by theory, it is here proposed that non-ionic detergents enhance the hydrophobicity of the affinity matrix to reduce non-specific binding of substantially unmethylated polynucleotides. One or more non-ionic polymeric detergents characterized by an uncharged hydrophilic head group such as Triton® X (Union Carbide Corp., Midland, Mich.), Brij® (Uniqema Americas LLC, Wilmington, Del.), Nonidet™ P-40 (Shell Brands International, Zug, Switzerland), or preferably Polysorbate (polyoxyethylene sorbitan monooleate) (Tween®, Uniqema Americas LLC, Wilmington, Del.) such as Tween 20, Tween 80, Tween 100 can be used at a concentration of less than 1%, more particularly at a concentration of less than 0.5%.

The use of non-ionic detergents and salt as described above resulted in a significant reduction in non-specific absorption of unmethylated CpG polynucleotides to MBD beads.

(d) Volume of Beads

The amount of beads that provides the desired effect of enrichment was tested in a suitable assay such as described in Example 3. It was shown in the example under the conditions described that 20 µl-40 µl of beads (4 µg-8 µg of MBD2a-Fc loaded on 200 µg-400 µg protein A-coated magnetic beads) were optimal for binding 250 ng DNA.

(e) Size of Polynucleotides

Enrichment of target or non target polynucleotides is preferably achieved with large molecular weight polynucleotide molecules having a size in the range of about 10 kb-100 kb, for example, polynucleotides having a size in the range of about 10 kb-20 kb. Methods of purifying DNA from cells prior to enrichment are known in the art. It is preferable to use methods that do not cause shear hence sonication or nebulization should be avoided. Instead, it is preferable to lyse the cells and use proteinase K followed by gentle organic extraction procedures (using chloroform and phenol (or ethanol) for phase separation and precipitation with ethanol) and/or a sizing column purification and/or agarose preparative gel electrophoresis (Sambrook, et al., *Molecular Cloning: A Laboratory Manual*, 3rd ed. pp. 6.4-6.12, Cold Spring Harbor Lab Press, Cold Spring Harbor, N.Y., (2001)).

All references cited herein, are hereby incorporated by reference.

EXAMPLES

Example 1

Adaptation of MBD Beads for Use in Enrichment of Unmodified DNA

MBD beads were obtained from NEB, Ipswich, Mass. (catalog #E2600).

The DNA was prepared by lysis of cells and chloroform-phenol extraction resulting in reduced DNA shear compared with sonication and provided fragments of at least 10 kb-20 kb in length, preferably at least 20 kb.

Titration of salt concentration: 250 ng of input purified DNA (from HeLa or *E. coli*) was incubated with 40 µl of MBD beads in a buffer containing 10 mM Tris, pH 7.5, 1 mM EDTA, 1% Triton X100, 0.1% Tween 80 (Polysorbate 80, J. T. Baker, Phillipsburg, N.J.), and increasing concentrations of NaCl (50 mM to 450 mM). The samples were incubated at room temperature for ten minutes after which the MBD beads were separated from the rest of the sample in the presence of a magnet external to the reaction vessel. The supernatant from each sample was loaded on to a 1% agarose gel, and assayed by ethidium bromide staining. FIG. 2 shows that Hela DNA was effectively removed from the supernatant by MBD beads at all NaCl concentrations, while the *E. coli* DNA remained in the supernatant.

Volume of beads: 250 ng of various purified genomic DNAs from mammalian cell lines (Hela, Jurkat, HCT 116, 3T3) and a normal, non-cancer fetal lung fibroblast cell line (IMR 90) were incubated with 20 µl or 40 µl MBD beads or beads coated with protein A only (20 µl MBD beads=4 µg MBD2a-Fc loaded on 200 µg protein A-coated magnetic beads, 40 µl MBD beads=8 µg MBD2a-Fc loaded on 400 µg Protein A-coated magnetic beads); (Stock Protein A magnetic beads (NEB) have a concentration of 10 mg/ml. Stock MDB2a-Fc have a concentration of 2 mg/ml (NEB).

Samples were incubated for 15 minutes, the supernatants removed, loaded on a 1% agarose gel, and assayed by SYBR green DNA stain. Effective removal of the DNA from the supernatant was achieved when 40 µl of the MBD beads was used in the reaction. Effective removal of the IMR 90 DNA was seen at 20 µl of beads.

Example 2

Efficacy of Separation of Mammalian DNA from Prokaryotic DNA

A mixture of DNAs (about 250 ng total DNA) consisting of a 50:50 mixture of mammalian DNA (human Jurkat) and bacterial DNA (*E. coli* strain ER 1506) of at least 20 kb in length was added to 40 µl MBD beads (200 µg/ml) prepared as described above and incubated for about 10 minutes. The sample tube was then placed on a magnetic rack for 5 minutes to concentrate MBD beads bound to double-stranded CpG-methylated DNA.

The supernatant containing the prokaryotic, viral or metagenomic DNA was carefully removed, leaving behind the eukaryotic or human DNA which adhered to the MBD beads. This DNA was extracted from the MBD beads using heat and Tris buffer containing proteinase K. The supernatant DNA was analyzed on a 1% agarose gel.

Figure 5:
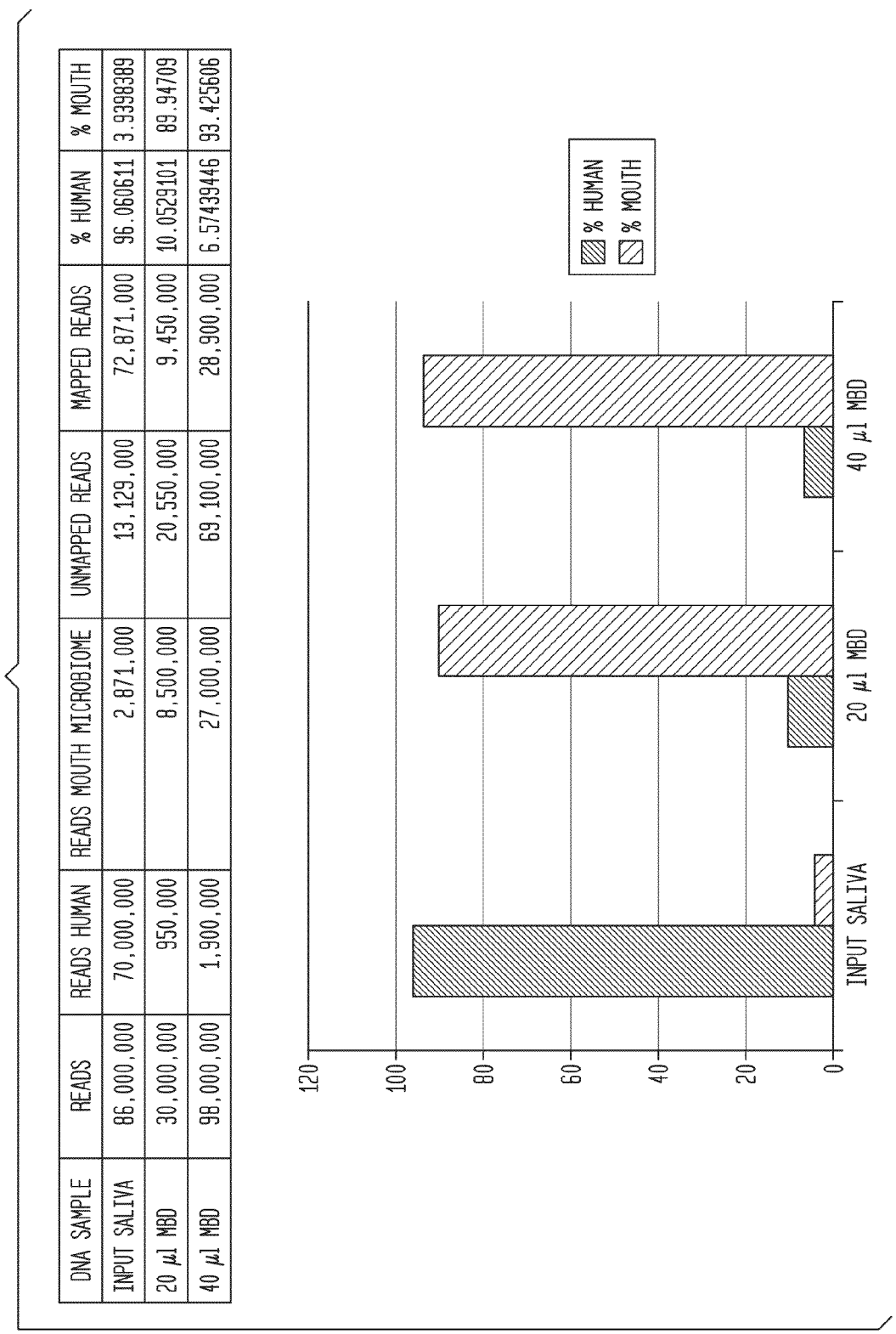
FIG. 5 shows the results of SOLiD™ 4 sequencing of purified DNA from a human saliva sample (Life Technologies, Carlsbad, Calif.). In the absence of MBD beads, the input DNA sample showed that 96% of the DNA reads aligned to human, while only 4% of the DNA sequencing reads aligned to a mouth microbiome database (Human Oral Microbiome Database (HOMD) (www.HOMD.org)); (Chen et al., *Database (Oxford)*. doi: 10.1093/database/baq013 (2010)). After enrichment with 20 µl MBD beads, the supernatant contained 10% of the DNA reads aligned to human and 90% of the sequence reads aligned to the HOMD. After treatment with 40 µl MBD beads, the supernatant contained 6.5% of the reads aligned to human DNA and 93.4% aligned to the HOMD.

The band on the agarose gel corresponding to the 20 kb unbound *E. coli* DNA from the supernatant was further analyzed using an Ion Torrent PGM sequencer so as to analyze the DNA present (see FIG. 5).

It was found that at least 95% of the human DNA (CpG-methylated) remained bound to the magnetic bead matrix while the bacterial DNA, which was not CpG-methylated, remained in the supernatant with recovery rates of greater than 95%.

Example 3

Analysis of Human Saliva for Microbial Genomes

Any method for the purification of RNA-free and protein-free genomic DNA can be used such as, for example, proteinase K treatment followed by phenol/chloroform extraction and ethanol precipitation, lysozyme digestion, Qiagen (Valencia, Calif.) column preparation (for genomic DNA) or other methods. Sonication, nebulization, chaotropic salts, enzymatic treatment, rough handling, or any other procedure that would cause DNA shear were avoided as separation of microbial DNA from mammalian DNA is optimal when the fragments of DNA are greater in size than 10 kb-20 kb and do not contain small molecular weight fragments (Sambrook, et al., *Molecular Cloning: A Laboratory Manual*, 3rd ed. pp. 6.4-6.12, Cold Spring Harbor Lab Press, Cold Spring Harbor, N.Y., (2001)). The DNA quality and quantity extracted from saliva can be determined by agarose gel electrophoresis of the sample alongside a DNA marker (2-log DNA ladder, NEB# N3200S, Ipswich, Mass.).

In this example, normal human saliva was acquired from Innovative Research (Novi, Mich.). 250 ml of saliva was added to 10 µl 1M Tris-HCL pH. 7.5, 5 µl 500 mM EDTA, 5 µl 20% SDS, 3 µl 20 mg/ml proteinase K (NEB# P8102S, Ipswich, Mass.), and incubated at 50° C. for 2 hours and ethanol-extracted. The pellet was air-dried, suspended in 25 mls of buffer (10 mM Tris, 1 mM EDTA, 100 µl RNaseA (10 mg)) and incubated at 37° C. for 1 hour. The released product was extracted with Tris-EDTA equilibrated phenol, once with dichloromethane, and 2 volumes ethanol (ETOH) were added. The product was then spun and the pellet air-dried as before and resuspended in 250 µl TE to give a final concentration of 150 µg/ml, 37.5 µg total.

Agarose gel analysis revealed ~50% of DNA was degraded below 10 kb. To further purify the DNA and enrich for high molecular weight fragments, the sample was loaded on a 1% low melt agarose gel plus 1×SYBR Safe DNA Gel Stain (Life Technologies, Carlsbad, Calif.). The large ~10-15 kb band was cut out of the gel, heated to 50° C., and 10 units Beta Agarase I (NEB #M0392S, Ipswich, Mass.), plus 100 µl 10× reaction buffer, in a total volume of 1 ml, was added to the sample and incubated at 42° C., for 30 minutes. 2 volumes of ETOH was added to the sample, spun, dried, and suspended in TE as above.

The above procedure was repeated on a second 250 ml pooled saliva sample of the same lot number and the two purified DNA samples were combined and the DNA concentration adjusted to 70 µg/ml; total yield was 40 µg.

The purified human saliva DNA described above was mixed with MBD beads in the following ratio: 250 ng DNA to 20 µl of MBD beads, or 40 µl MBD beads. Without the use of MBD beads to enrich for prokaryotic DNA, the DNA sample showed that 96% of the DNA reads aligned to human, while only 4% of the DNA sequencing reads aligned to HOMD.

Figures 1, 6A:
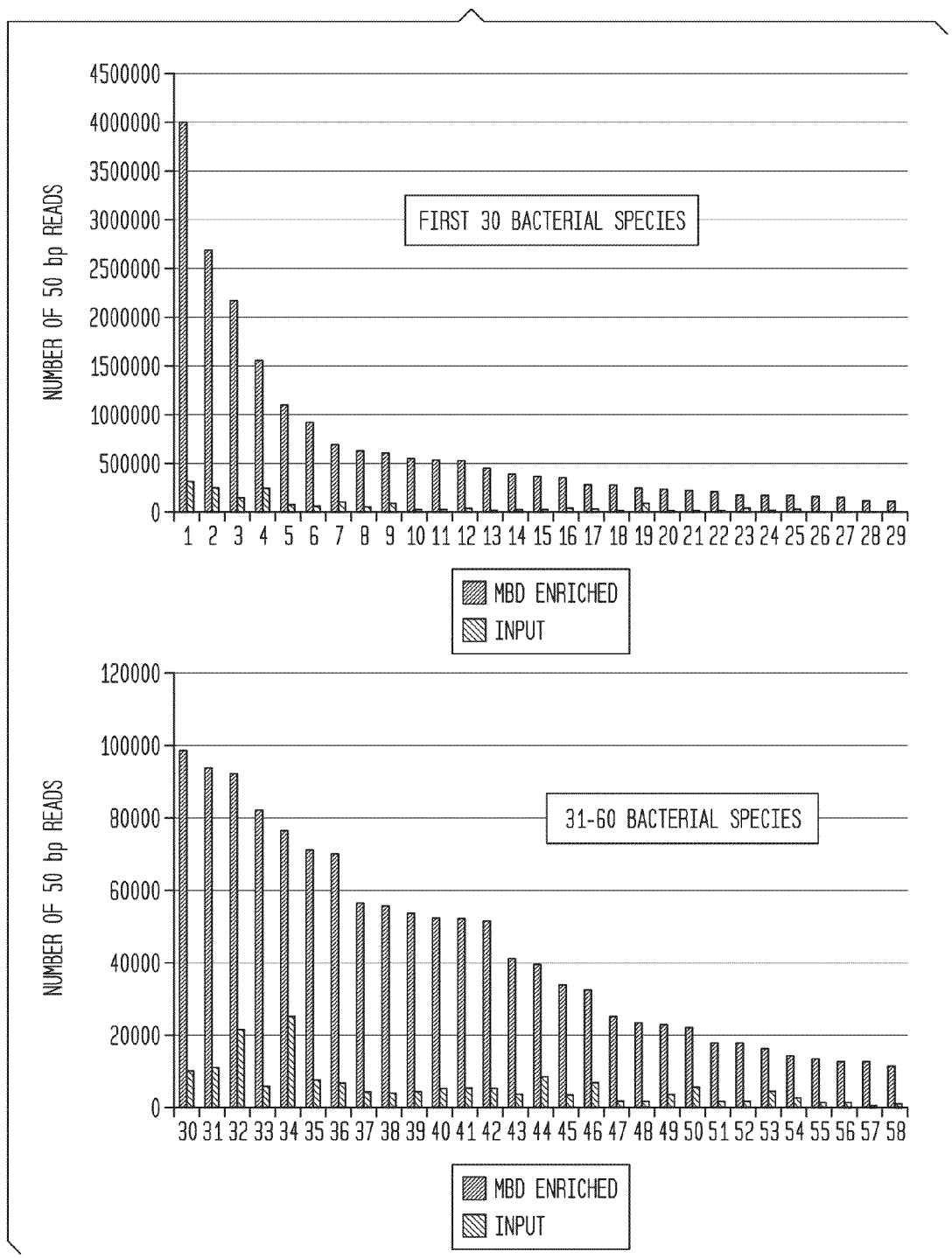
Figures 2, 6A:
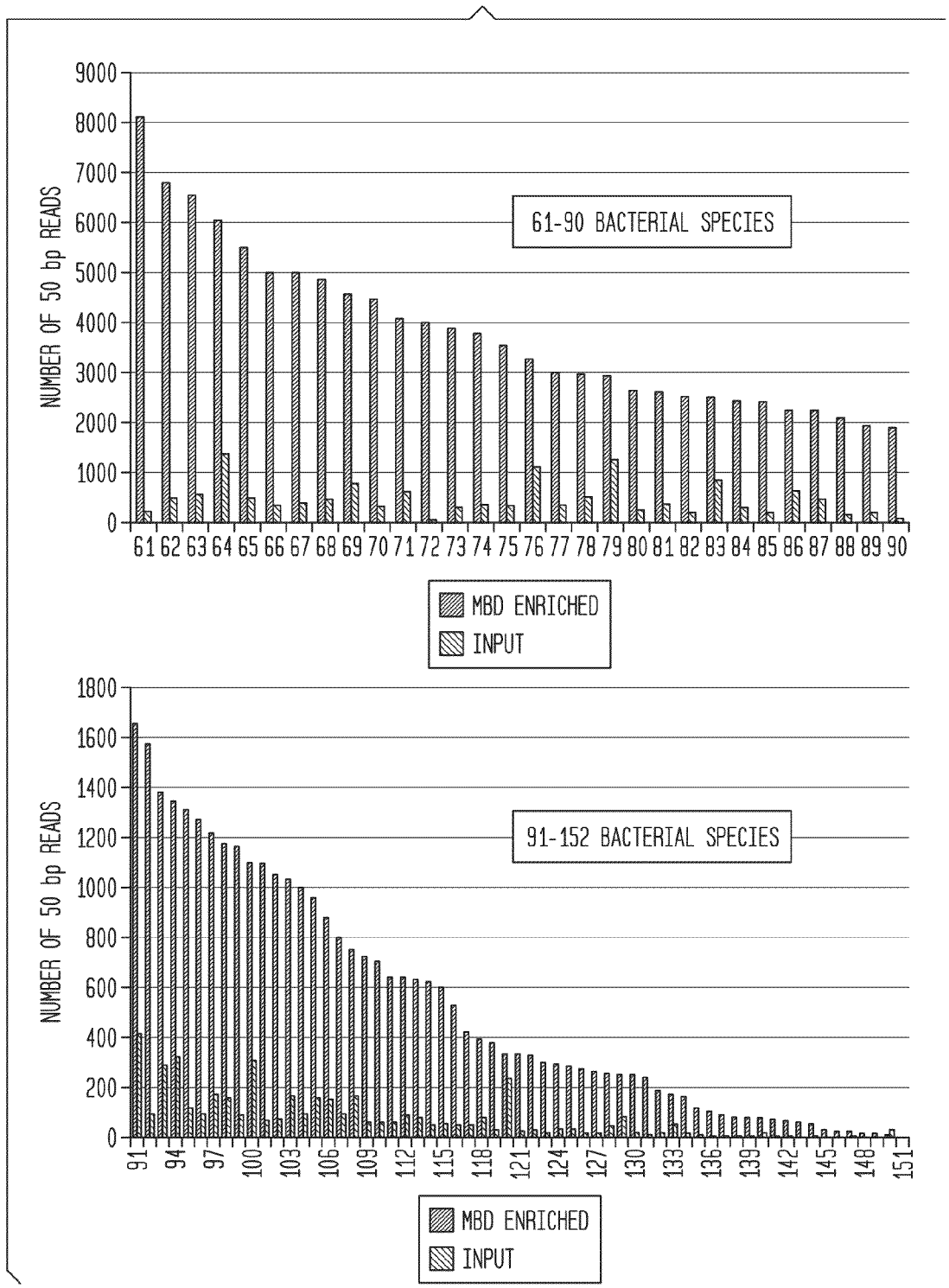
Figure 7:
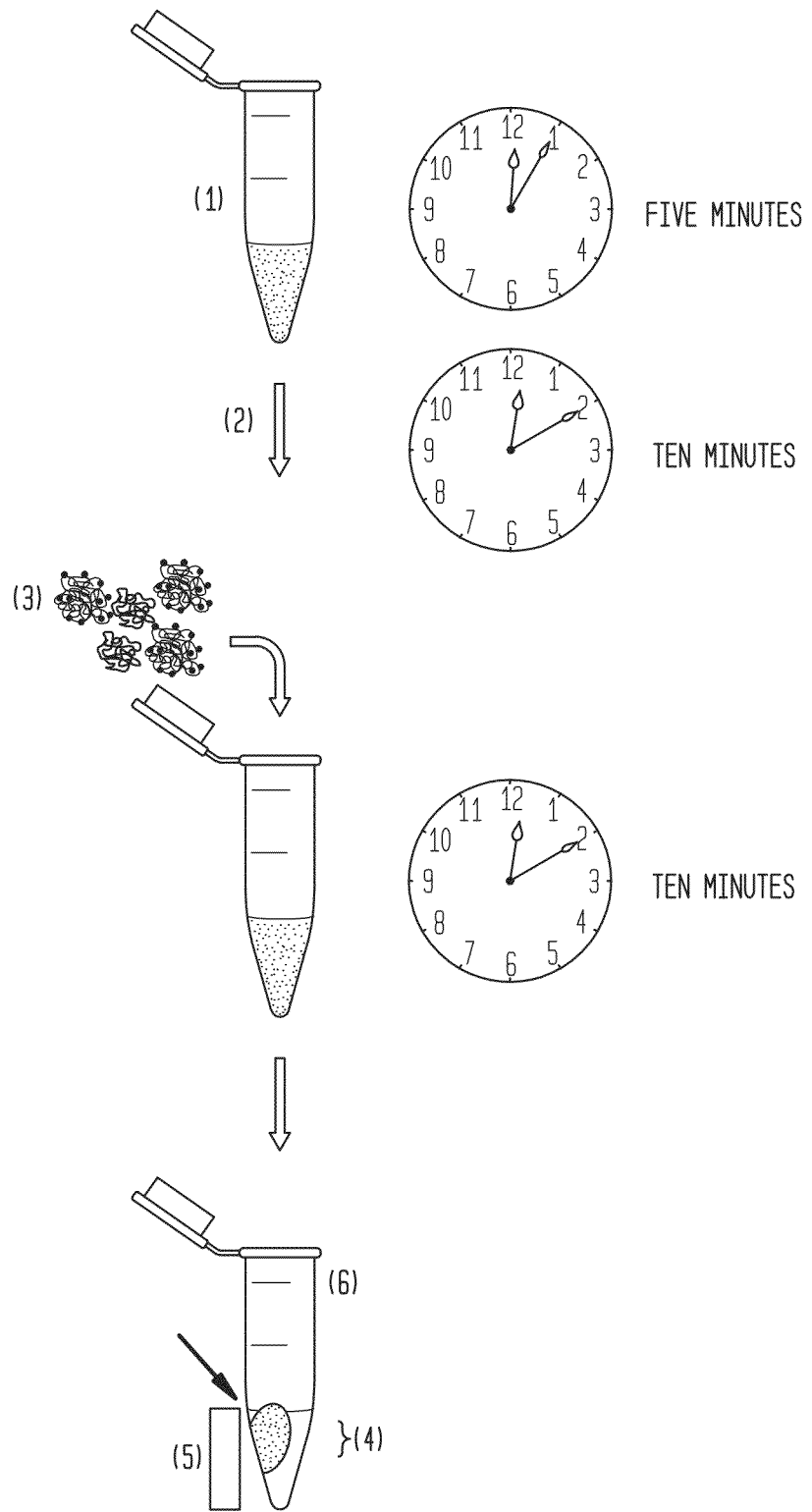
FIG. 7 shows a workflow for enrichment of mitochondrial DNA. (1) refers to the addition of MBD-Fc protein to protein A magnetic beads for a 5 minute incubation. (2) refers to a 2× wash of the beads over a 5 minute period; (3) refers to the addition of genomic DNA mixture to beads over a ten minute period; (4) refers to separation of eukaryotic genomic DNAs from magnetic beads after a ten minute incubation; (5) refers to a magnet; and (6) refers to prokaryotic or mitochondrial or chloroplast DNA in the supernatant.
Figure 8:
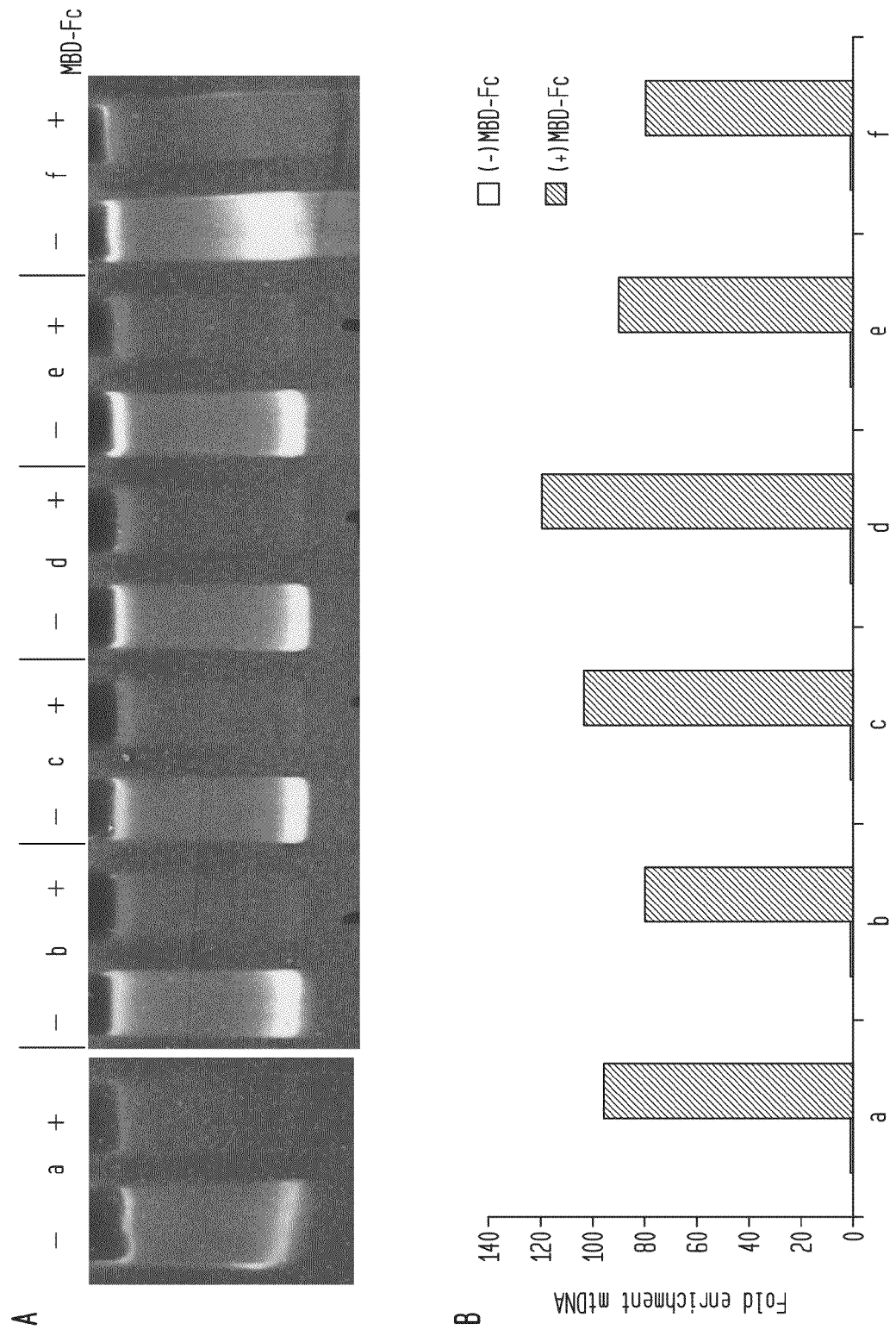
FIG. 8A-B shows the selective removal of human chromosomal DNA from six different tissue sources. The protocol in FIG. 7 was followed using cell DNA that was extracted so as to form a band of 10-20 Kb fragments on a 10% polyacrylamide gel. Removal of chromosomal DNA by MBD was determined using 250 ng of the DNA added to 50 ul of MBD-Fc beads.
Figure 9:
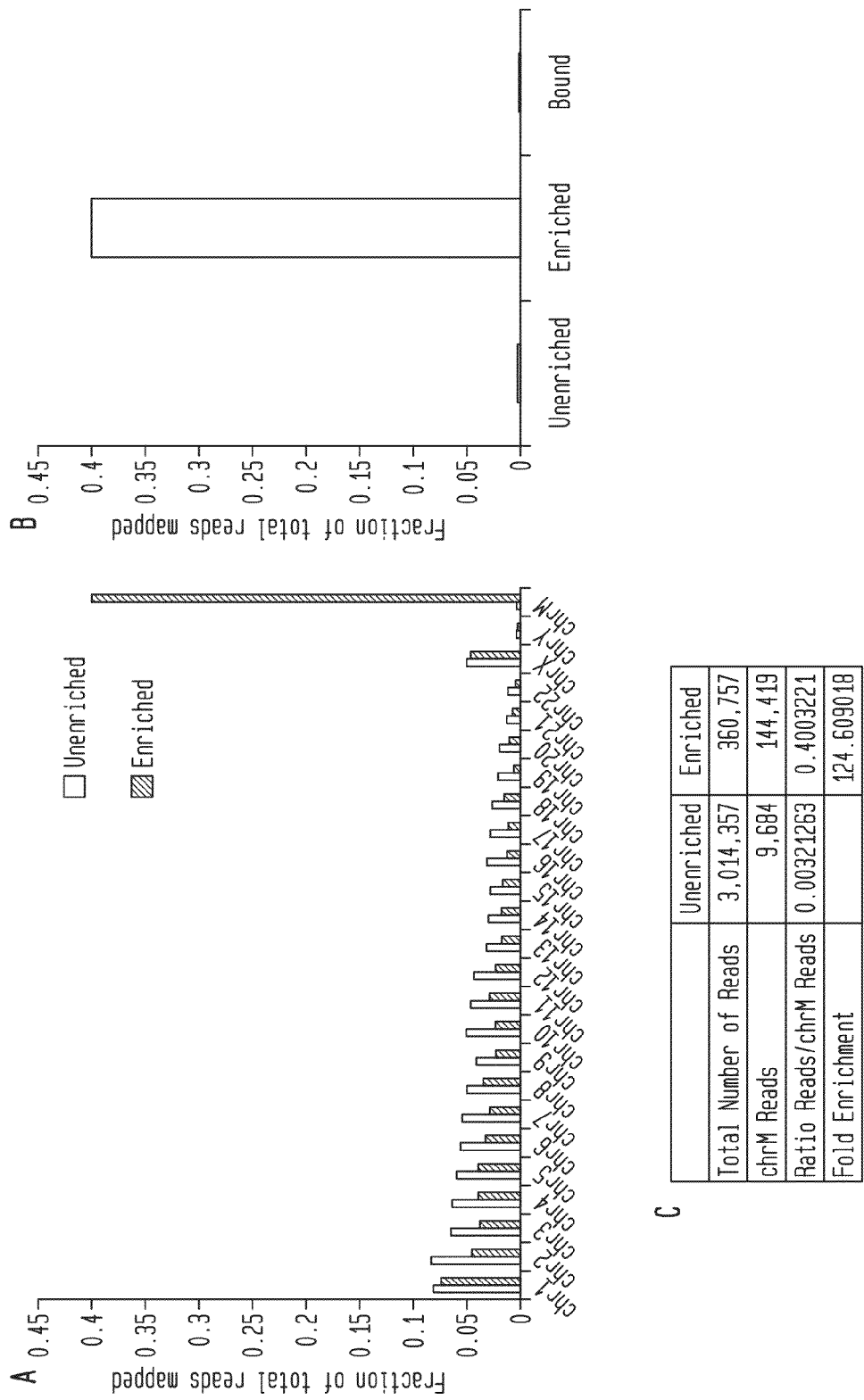
FIG. 9A-C shows that at least 40% of the DNA in the supernatant is mitochondrial DNA where a cell lysate contains only about 0.3% mitochondrial DNA in total cell DNA without enrichment.
Figure 10A:
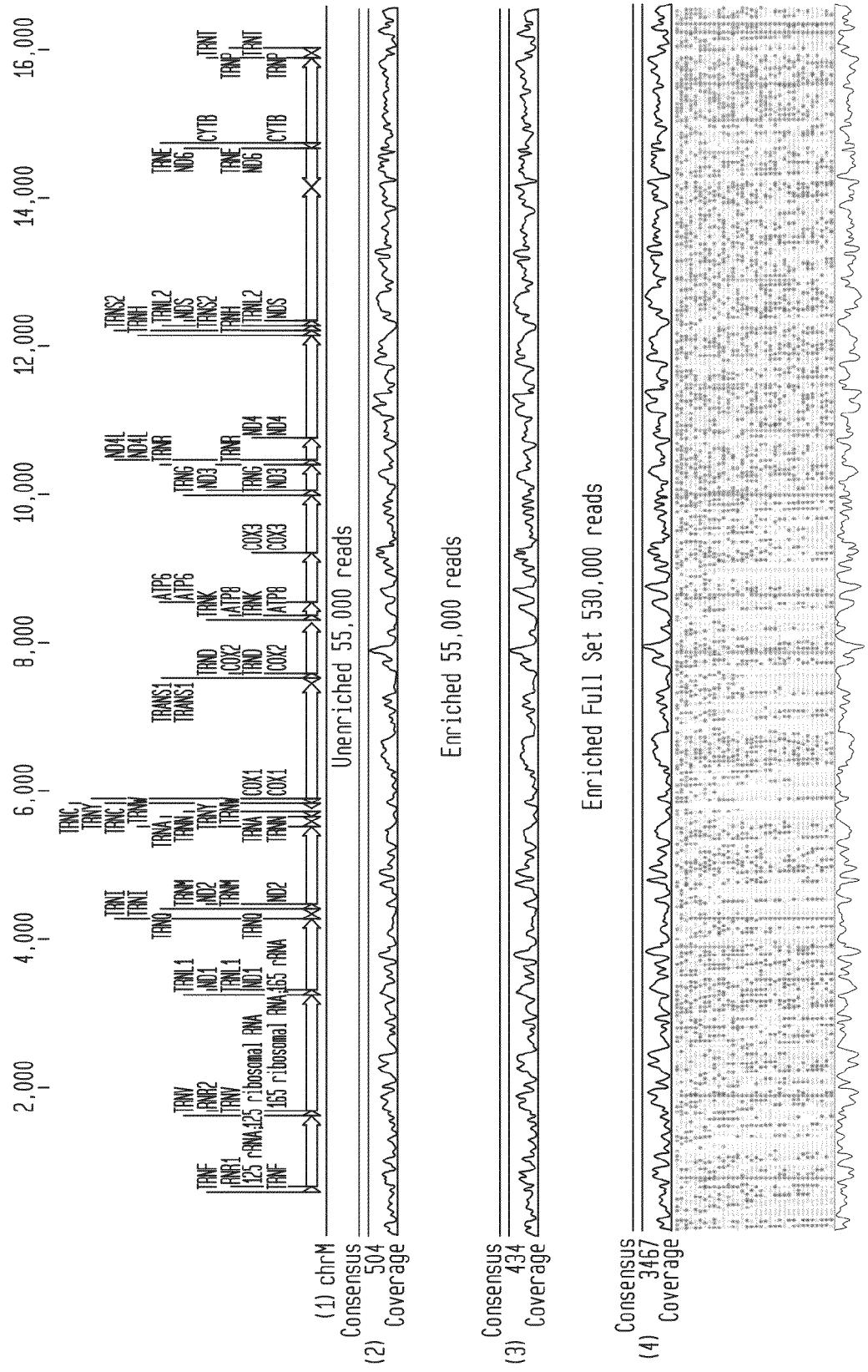
FIG. 10A-B show the results of sequencing DNA from the male human leukocyte buffy coat fraction of human blood using a SOLiD™ sequencing platform (Life Technology Inc, California). The enrichment method does not reveal any detectable bias with respect to AT or GC rich sequences between unenriched and enriched datasets.
Figure 10B:
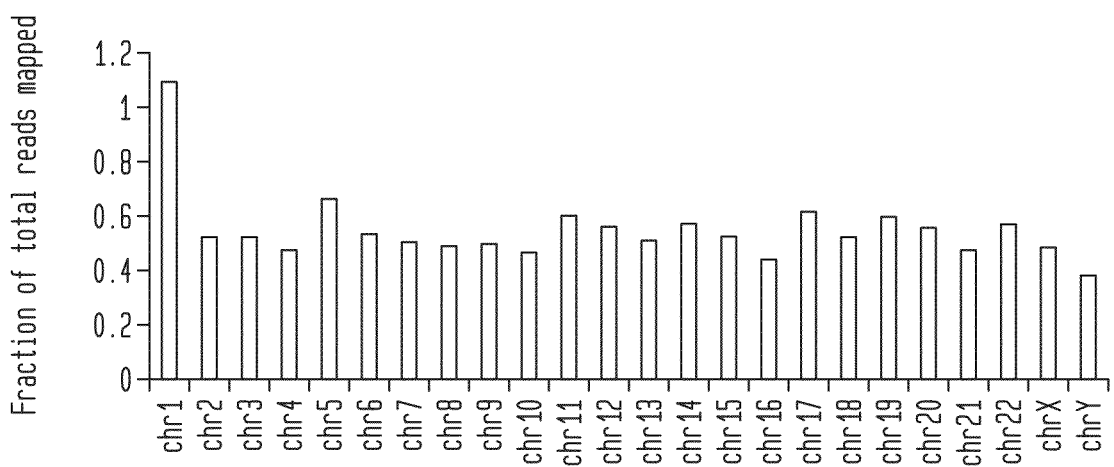
Figure 11:
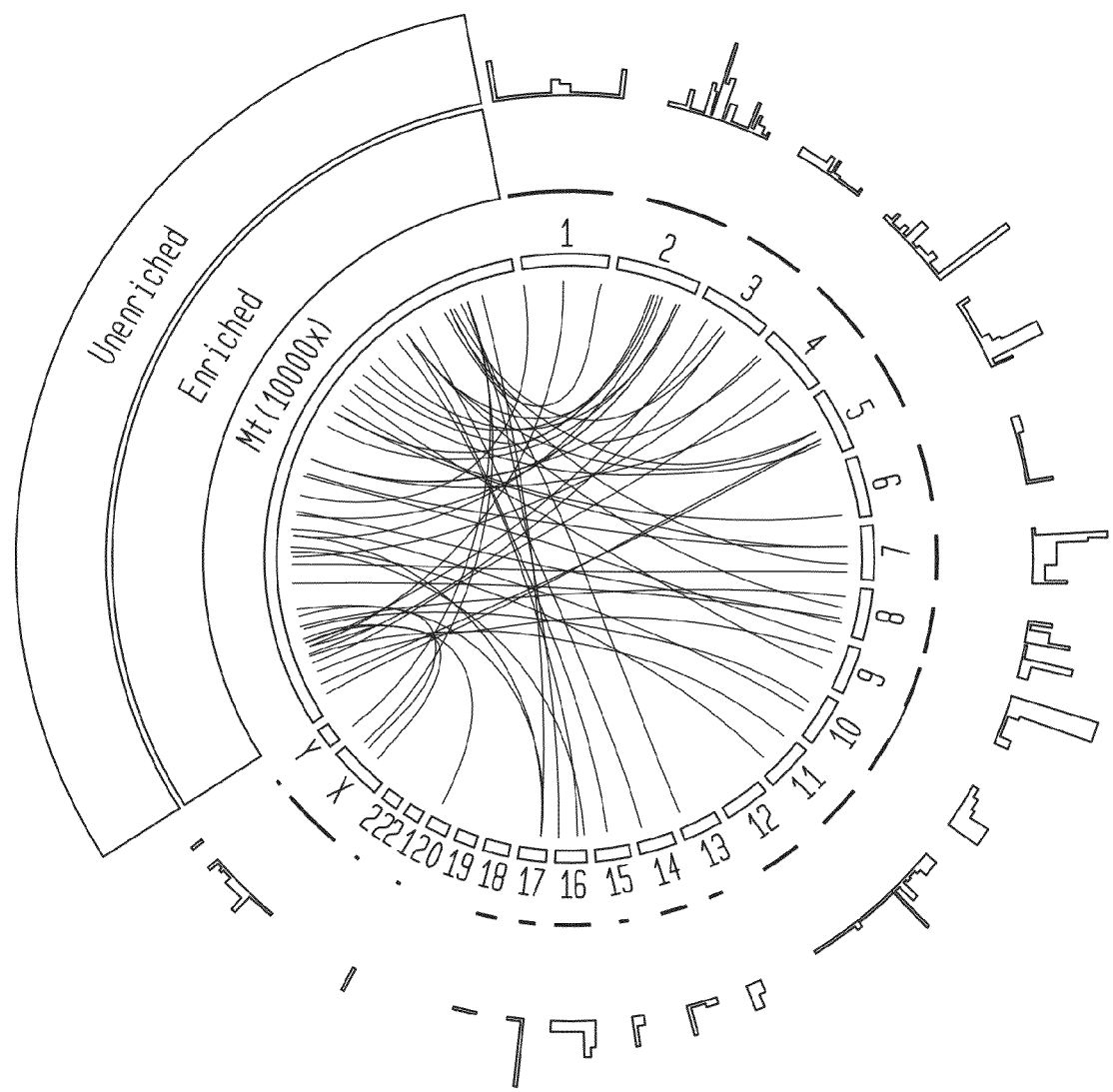
FIG. 11 shows how embodiments of the method providing enrichment of mitochondrial DNA removes complications arising from mitochondrial sequences that are transposed into chromosomal DNA (where they are likely CpG methylated) and which confuse traditional analyses of mitochondrial DNA significantly contaminated by chromosomal DNA. Here, sequences identified as mitochondrial sequences that are not chromosomal transposed sequences resulting from contamination are shown graphically using bioinformatics and quantitative analysis using 173 million SOLiD 4 reads of unenriched and enriched samples. The fraction of reads overlapping with chromosomal reads and having mirochondrial sources known as NUMTs are shown by black lines using Bowtie 2 and Bedtools bioinformatics tools (Lascaro, et al., *BMC Genomics*, 9, 267. doi:10.1186/1471-2164-9-267 (2008); Langmead, et al., *Nature Methods*, 9(4):357-359. doi:10.1038/nmeth.1923 (2012); and Quinlan, et al., *Bioinformatics*, 26(6):841-842 doi:10.1093/bioinformatics/btq033 (2010)). Enrichment dramatically reduced undesired reads on NUMTs and evenly focused reads on the mitochondrial regions of interest.

After enrichment with 20 µl MBD beads, 10% of the DNA reads aligned to human, and 90% of the reads aligned to HOMD. After treatment with 40 µl MBD beads, 6.5% of the reads aligned to human, and 93.4% aligned to HOMD (FIG. 6A-1 and 6A-2).

Example 4

Enrichment of Human Mitochondrial DNA

Human mitochondrial DNA is a circular DNA molecule of about 16.5 kb. It encodes 37 genes: 13 for subunits of respiratory complexes I, III, IV and V, 22 for mitochondrial tRNA (for the 20 standard amino acids, plus an extra gene for leucine and serine), and 2 for rRNA. One mitochondrion can contain two to ten copies of its DNA (Chan, *Cell*, 125 (7): 1241-1252 (2006). doi:10.1016/j.cell.2006.06.010.)). Many diseases are associated with mitochondrial DNA defects and so it is desirable to enrich for mitochondrial DNA. Using the methods described herein, two input samples (4.75×105 bases) were compared with four enriched supernatant samples (1.6×105 bases) and two pellet samples (1.5×106 bases) using IMR 90 DNA assayed on an Ion Torrent PGM System. DNA was extracted from human buffy coat blood, saliva, heart, brain, and a human fibroblast cell line were enriched for mtDNA. The enriched samples were used for sequencing All base reads were aligned to the human genome (hg19) using Bowtie 0.12 alignment software and a chromosome distribution was performed. It was found that the MBD supernatant sample had a 160-fold enrichment of mitochondrial DNA as compared to the input sample. Conversely, the pellet contained no detectable mitochondrial DNA.

This simple methodology can be used to analyze low-level mtDNA hetroplastic mutations from a variety of clinical samples in a cost-effective manner utilizing established Next-Gen sequencing platforms, as well as newer single molecule sequencing technologies.

---

What is claimed is:

1. A composition comprising:
   a mixture comprising eukaryotic chromosomal DNA and mitochondrial DNA, wherein the chromosomal DNA in the mixture has a median size of at least 10 kb,
   a matrix comprising a protein that comprises a methyl binding domain, wherein the protein is capable of selectively binding to methylated polynucleotides but not non-methylated polynucleotides, and
   a buffer containing effective amounts of a salt and a non-ionic detergent.

2. A composition, according to claim 1, wherein the effective amount of salt is 10 mM-800 Mm.

3. A composition according to claim 1, wherein the chromosomal DNA is bound to the matrix and a significant portion of the mitochondrial DNA is unbound in the buffer.

4. A composition according to claim 3, wherein the unbound mitochondrial DNA in the buffer is enriched by at least a 100 fold compared to the mitochondrial DNA in the mixture.

5. A composition according to claim 3, wherein less than 10% of the chromosomal DNA in the cell DNA is unbound in the buffer.

6. A composition according to claim 3, wherein less than 10% of the mitochondrial DNA in the mixture is bound to the matrix.

7. A composition according to claim 3, wherein at least 90% of the mitochondrial DNA and less than 10% of chromosomal DNA is unbound in the buffer.

8. A composition according to claim 1, wherein the matrix comprises magnetic beads.

9. A composition according to claim 1, wherein the methyl-binding domain (MBD) is selected from the group consisting of UHRF1(SRA), CXX1, DNMT1, MBD and methyl-binding variants thereof.

10. A composition according to claim 1, further comprising chloroplast DNA.

11. A composition according to claim 10, wherein at least 90% of the chloroplast DNA is unbound in the buffer.

12. A method for enriching cellular mitochondrial DNA from a cell sample, comprising:
   (a) obtaining a composition according to claim 1;
   (b) permitting the chromosomal DNA to bind to the matrix; and
   (c) obtaining an enriched preparation of mitochondrial DNA in a unbound fraction.

13. A method according to claim 12, further comprising determining the fraction of the mitochondrial DNA and chromosomal DNA in the unbound fraction.

14. A method according to claim 12, further comprising, sequencing a part of the entire mitochondrial DNA.

15. A method according to claim 12, further comprising perfoming a genetic analysis of the mitochondrial DNA.

16. A method according to claim 12, further comprising perfoming a genetic analysis of single nucleotide polymorphisms in the mitochondrial DNA.

17. A method according to claim 15, further comprising: analyzing the mitochondrial DNA for oxidative damage.

18. A method according to claim 12, wherein the methyl-binding domain (MBD) is selected from the group consisting of UHRF1(SRA), CXX1, DNMT1, MBD and methyl-binding variants thereof.

19. A method according to claim 12, wherein the matrix comprises magnetic beads.

20. A method according to claim 19, wherein the magnetic beads are coated with protein A bound to MBD2a-Fc.

21. A method for detecting oxidative damage in mitochondrial DNA, comprising:
(a) enriching mitochondrial DNA using the method of claim 12;
(b) identifying a change in oxidation status of methylcytosine to hydroxymethylcytosine in chromosomal DNA bound to the MBD as an indicator; and
(c) analyzing the mitochondrial DNA in the unbound fraction for reactive oxygen damage.

* * * * *

SEQUENCE LISTING

```
<160> NUMBER OF SEQ ID NOS: 3

<210> SEQ ID NO 1
<211> LENGTH: 86
<212> TYPE: PRT
<213> ORGANISM: human
<220> FEATURE:
<221> NAME/KEY: MISC_FEATURE
<222> LOCATION: (1)..(86)
<223> OTHER INFORMATION: 1-86 amino acid residues correspond to 144-230
      in Human MBD2

<400> SEQUENCE: 1

Glu Ser Gly Lys Arg Met Asp Cys Pro Ala Leu Pro Pro Gly Trp Lys
1               5                   10                  15

Lys Glu Glu Val Ile Arg Lys Ser Gly Leu Ser Ala Gly Lys Ser Asp
            20                  25                  30

Val Tyr Tyr Phe Ser Pro Ser Gly Lys Lys Phe Arg Ser Lys Pro Gln
        35                  40                  45

Leu Ala Arg Tyr Leu Gly Asn Thr Val Asp Leu Ser Ser Phe Asp Phe
    50                  55                  60

Arg Thr Gly Lys Met Met Pro Ser Lys Leu Gln Lys Asn Lys Gln Arg
65                  70                  75                  80

Leu Arg Asn Asp Pro Leu
                85

<210> SEQ ID NO 2
<211> LENGTH: 14
<212> TYPE: PRT
<213> ORGANISM: artificial sequence
<220> FEATURE:
<223> OTHER INFORMATION: flexible linker

<400> SEQUENCE: 2

Ala Ala Ala Asp Pro Ile Glu Gly Arg Gly Gly Gly Gly
1               5                   10

<210> SEQ ID NO 3
<211> LENGTH: 232
<212> TYPE: PRT
<213> ORGANISM: human
<220> FEATURE:
<221> NAME/KEY: MISC_FEATURE
<222> LOCATION: (1)..(232)
<223> OTHER INFORMATION: Amino acid residues 1-232 correspond to the Fc
      region (residues 99-330) of the human IgG1

<400> SEQUENCE: 3

Asp Pro Lys Ser Ser Asp Lys Pro His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
```

-continued

```
                35                  40                  45
Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Ala Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```